US00PP16444P3

(12) United States Plant Patent
Tate

(10) Patent No.: US PP16,444 P3
(45) Date of Patent: Apr. 11, 2006

(54) WILLOW OAK TREE NAMED 'RT3'

(50) Latin Name: *Quercus phellos*
Varietal Denomination: RT3

(76) Inventor: Ray Tate, 435 Ray's Church Rd., Bishop, GA (US) 30621

( * ) Notice: Subject to any disclaimer, the term of this patent is extended or adjusted under 35 U.S.C. 154(b) by 140 days.

(21) Appl. No.: 10/666,392

(22) Filed: Sep. 19, 2003

(65) Prior Publication Data

US 2005/0066399 P1 Mar. 24, 2005

(51) Int. Cl.
*A01H 5/00* (2006.01)

(52) U.S. Cl. ..... Plt./225

(58) Field of Classification Search ..... Plt./225
See application file for complete search history.

*Primary Examiner*—Anne Marie Grunberg
*Assistant Examiner*—Annette H Para
(74) *Attorney, Agent, or Firm*—Polster, Lieder, Woodruff & Lucchesi

(57) ABSTRACT

A Willow Oak tree named 'RT3' and distinguished by having a narrow, upright, densely branched habit with a central leader and also capable of being reliably reproduced from vegetative cuttings.

6 Drawing Sheets

Latin name of the genus and species of the plant claimed: *Quercus phellos*.
Variety denomination: 'RT3'.

BACKGROUND OF THE INVENTION

The present invention relates to a new and distinct variety of a Willow Oak tree (*Quercus phellos*) to which I have given the varietal name 'RT3'.

DISCOVERY

I discovered my new variety of Willow Oak tree in the Summer, 2000, growing in a landscaped area of a shopping center parking lot in Athens, Clarke County, Ga. The tree was growing among a group of cultivated Willow Oak trees which were planted at approximately the same time as my tree. The manager of the shopping center confirmed to me that all of the trees in the parking lot were installed as 2" field-grown nursery trees in 1986 by a professional landscaper. The nursery source of the trees is unknown, so the age of my tree cannot be known with complete certainty. However, a 2" field grown tree would probably be approximately four (4) years old from a seed. It can therefore be assumed that my tree is approximately 22 years old.

PROPAGATION

'RT3' was asexually propagated at my direction in the summer, 2001. Propagation took place at my nursery in Bishop, Ga. from a cutting taken from a Willow Oak tree. The propagation and its resulting progeny have proven that my new variety has characteristics which are firmly fixed. Further, there observations have confirmed my new variety represents a new and improved variety of Willow Oak tree, as particularly evidenced by a narrow, upright, densely branched habit with a centered leader which can be readily propagated asexually.

UNIQUENESS

'RT3' was observed to have a narrow, upright, densely packed habit with a central leader. These characteristics distingish my new tree from other typical seedlings of Willow Oaks and known cultivars.

USE

'RT3' was observed for a period of time and is believed to be particularly useful in residential and commercial street plantings, lawns, parks, and other large areas, as well as smaller planting areas such as parking lots, and near buildings. The narrow habit of the 'RT3' Willow Oak makes it suitable for planting in areas which do not have sufficient space to accommodate a large-spreading tree typical of the species, such as around buildings in urban areas and commercial developments. The upright, dense branching habit and central leader of my 'RT3' Willow Oak is advantageous to growers because it requires less labor to produce a quality, saleable tree. My tree has further demonstrated its suitability to grow in urban areas by virtue of its current location. The tree is presently growing in a narrow, concrete island which is approximately four feet (4') wide, and flanked on both sides by parking lots. My new tree has survived and remained healthy in this location since it was planted sometime in 1986.

SUMMARY OF THE INVENTION

BACKGROUND

Seedling Willow Oaks have a spreading canopy which is often open in youth. A Willow Oak is a large, deciduous tree having a dense oblong-oval crown when the tree reaches maturity. On average, a Willow Oak reaches a height of 40'–60' and a width ranging from 30'–40'. The largest trees of the species will be on the order of 100' tall, and equally as wide. My new cultivar differs from the species in that it has a narrow, upright, densely branched habit with a central leader. The Willow Oak is native from New York to Florida, and west to Missouri, Oklahoma, and Texas. Willow Oak seedlings are grown commercially throughout the southeastern United States.

The tree does well in USDA Zones 5–9, and performs best in Zones 6–8. Willow Oaks are considered heat and drought tolerant, and one of the best oak trees for heat, drought, and humidity common throughout the Southeast; although the trees are also known to survive temperatures as cold as −25° F. in areas such as Cincinnati, Ohio. The species also does well in the more arid Midwestern portion of the country. Willow Oak trees are found growing in bottomlands, floodplains, and adjacent slopes. They prefer moist, well-drained soil, but adapt well to harsh conditions.

INDUSTRY REPRESENTATION

Cultivated Willow Oak is represented in the industry by seedling material. The species is typically pyramidal in youth, becoming spreading in maturity. As noted, the tree typically attains a height width and width of 40'–60' and has a height-to-width ratio of approximately 1.0.

To my knowledge, there are only two other clonally propagated Willow Oaks available to the industry. These are *Quercus phellos* 'QPSTA' U.S. Plant Pat. No. 13,677 Hightower®, and *Quercus phellos* 'QPMTF' U.S. Plant Pat. No. 15,217 Wynstar®. Both are recently introduced selections of Willow Oak.

Hightower® Willow Oak has a height-to-width ratio of 1.61, and its branching pattern is significantly different from my new tree. On a Hightower® Willow Oak, secondary branches emerge at 50° angles from the trunk and flatten with age to 80°–90° angles from the trunk. The final branching habit is primarily horizontal in its appearance with a slight uprightness at the top of the tree as new branches emerge. These statements are supported by claims and images in the patent for Willow Oak 'QPSTA' U.S. Plant Pat. No. 13,677. Compared to the Hightower® Willow Oak, my new tree is more uprightly branching.

Wynstar® Willow Oak has a height-to-width ratio of 1.22 and a more horizontal branching habit than a Hightower® Willow Oak or my new tree. Branches emerge at 30° angles from the trunk and flatten with age to 80°–90° angles from the trunk. Images of the parent trees show a tendency for older branches to be slightly pendulous. Its branching habit is described as broad-spreading. A Wynstar® Willow Oak also has a lower branch density than the Hightower® Willow Oak or my new tree. These statements are supported by claims and images in the patent for Willow Oak 'QPMTF' U.S. Plant Pat. No. 15,217. Compared the to Wynstar® Willow Oak, my new tree is more uprightly branching and has a higher branch density.

After 22 years, my new tree is 35 feet tall and 17 feet wide (a height-to-width ratio of 2.06), making it significantly narrower than any other known willow oak cultivars or seedlings. Branches emerge at 20°–30° angles from the trunk and only flatten to 30°–40° angles from the trunk with age. My new tree also has significantly denser branching than any other known seedling or Wynstar® Willow Oak, as evidenced by FIG. 1. In my experience, no other seedling or cultivar of Willow Oak has displayed the growth habit of my 'RT3' Willow Oak. My new tree is currently 12.59" in caliper at 4" above the ground. This caliper measurement is larger than 50% of the other trees planted at the same time at the same site. Since it was planted in 1986, the annual average caliper development has been about 0.59" per year. Nursery-grown Willow Oak trees in this area have an average annual caliper increase of about 0.75" to 1.00", and I expect my new tree to perform as well once grown in a nursery setting.

DESCRIPTION OF THE DRAWINGS (PHOTOGRAPHS)

The accompanying photographs depict the color of the tree and the foliage of my new variety as nearly as is reasonably possible to make the same in a color illustration of this character.

FIG. 1 depicts my Willow Oak tree 'RT3' in its summer habit. As shown in the Fig., my tree has a narrow, upright, densely branching habit and canopy. The photograph was taken in the Summer, 2003, when the tree was approximately 22 years old, approximately 35' tall, approximately 17' wide, and having a caliper of 12.59".

DETAILED DESCRIPTION OF INVENTION

Figure 1:
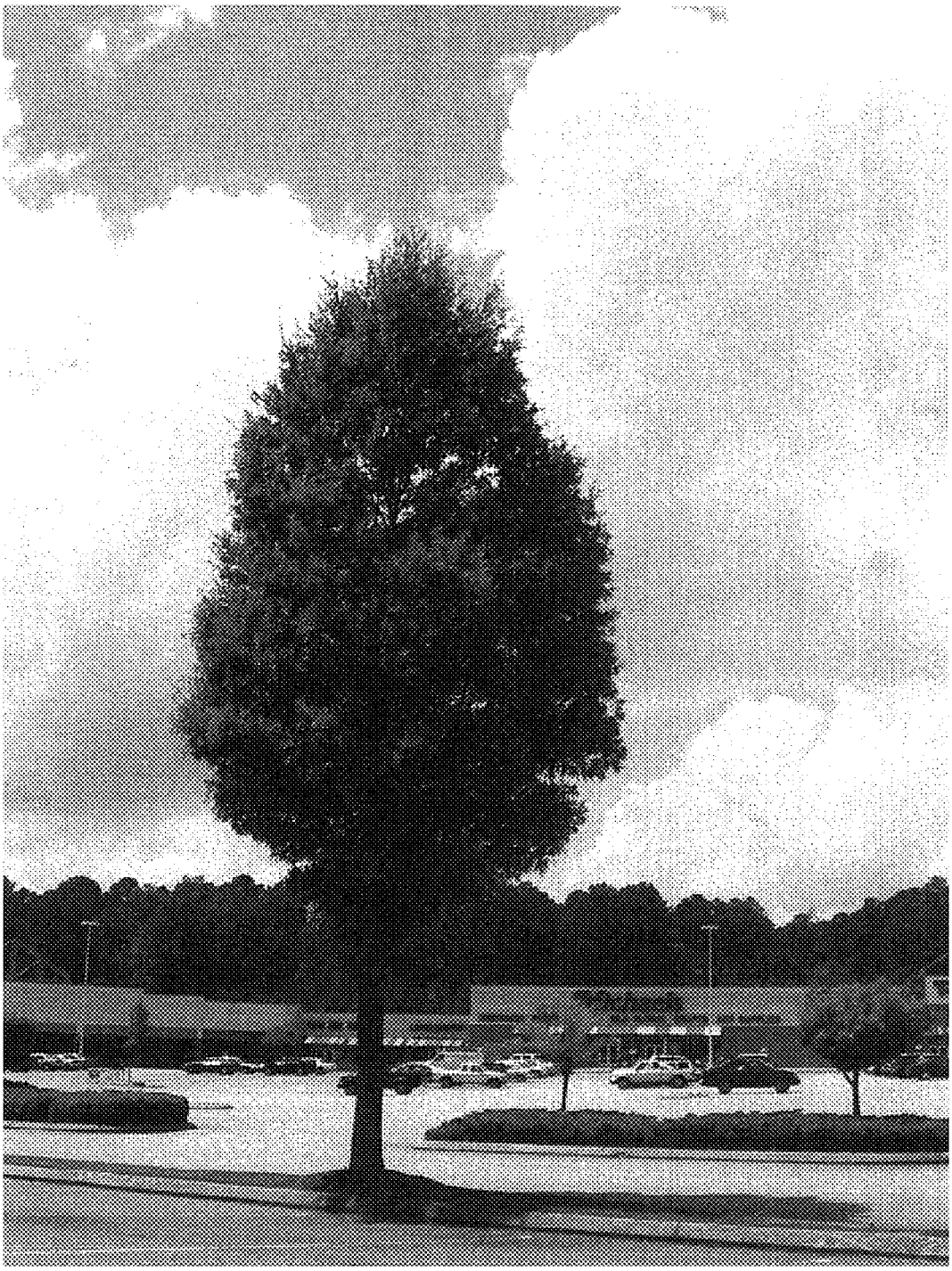
Figure 2:
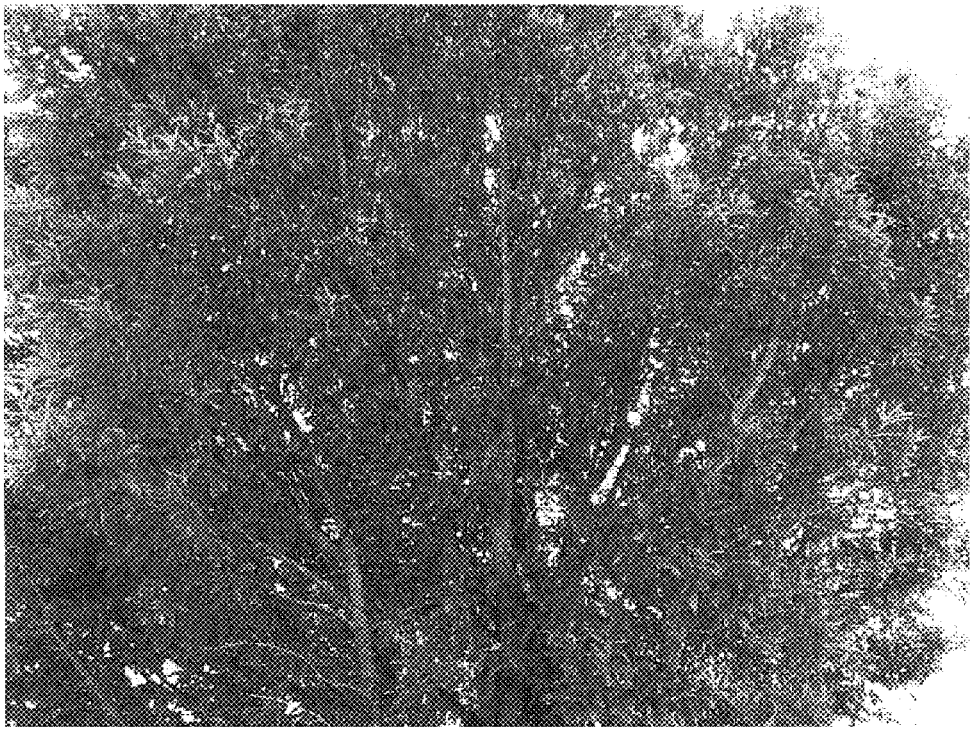
FIG. 2 depicts the branching habit of my Willow Oak tree 'RT3'.
Figure 3:
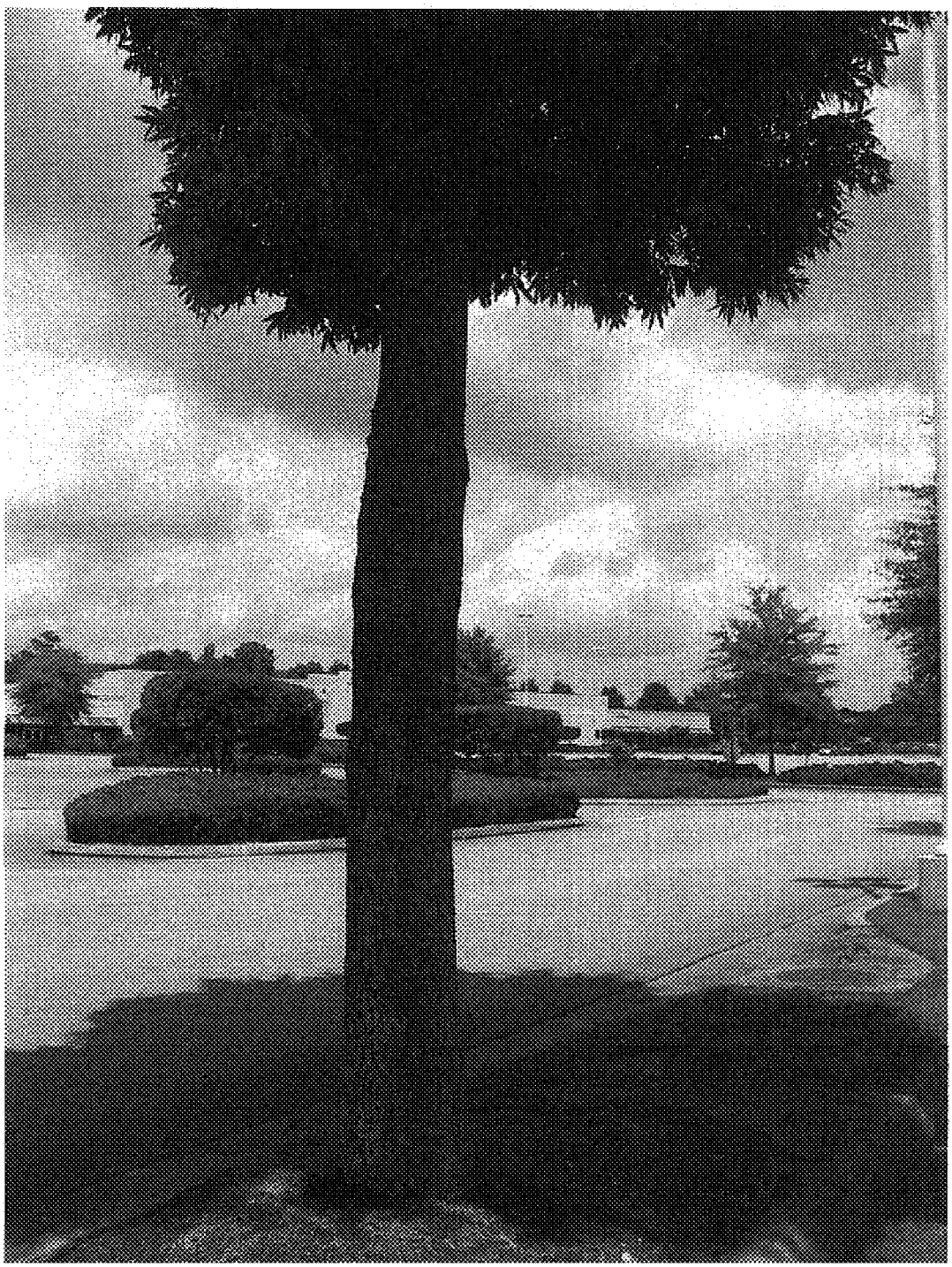
FIG. 3 depicts the trunk of my tree.
Figure 4:
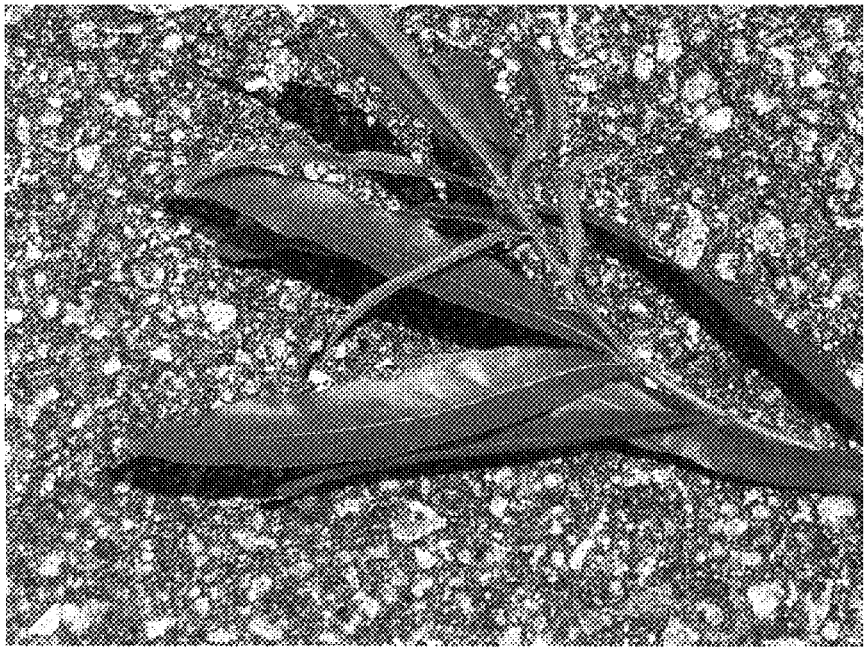
FIG. 4 depicts the upper leaf surface of my Willow Oak tree 'RT3'.
Figure 5:
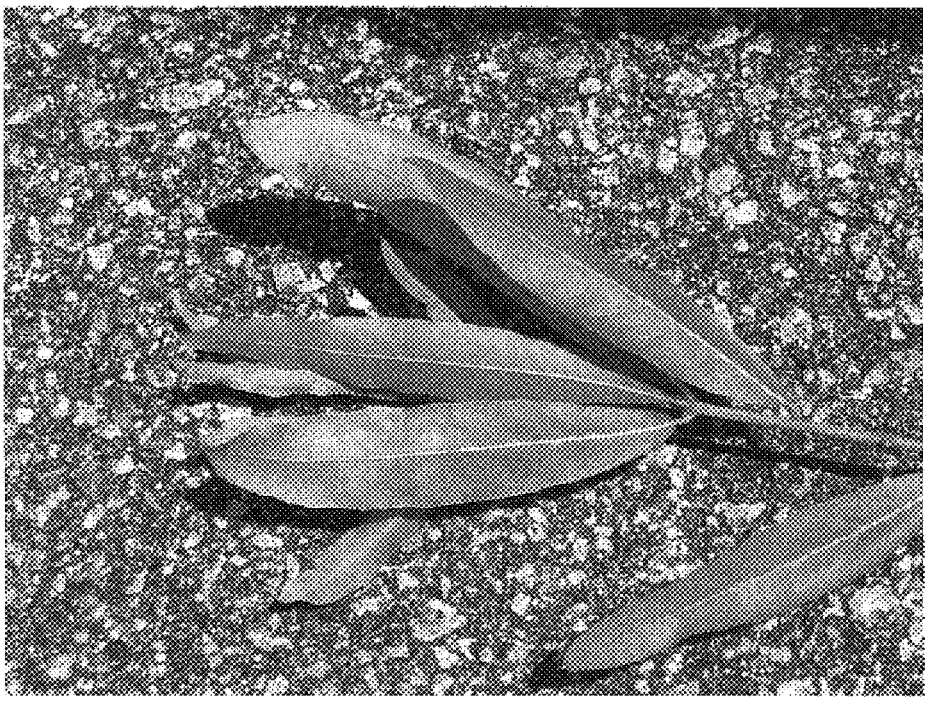
FIG. 5 depicts the underside or lower leaf surface of my tree.
Figure 6:
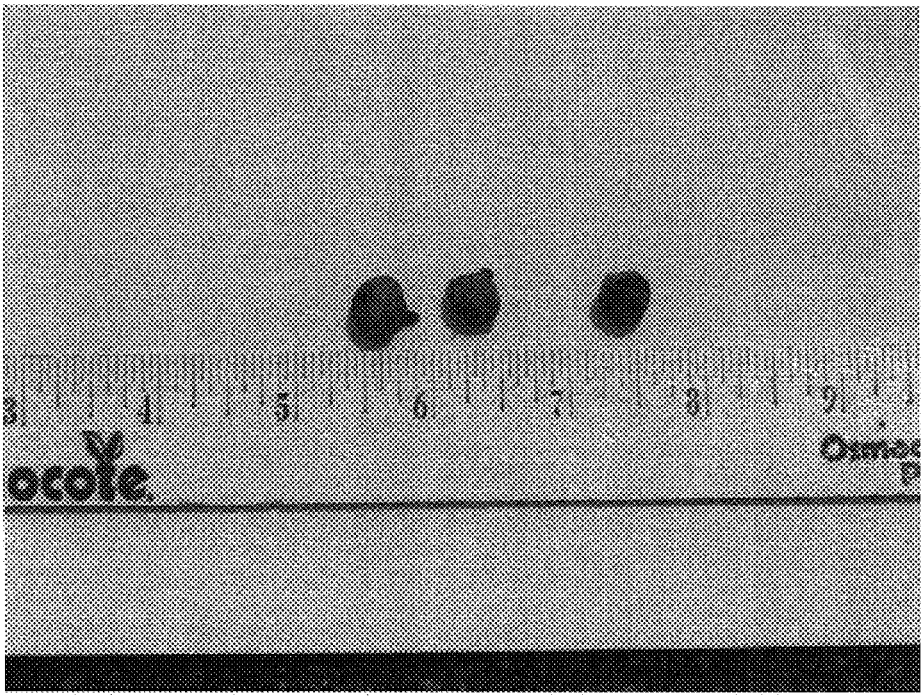
FIG. 6 depicts acorns and caps from my tree.

The following is a detailed description of my new variety of Willow Oak with color terminology in accordance with The Royal Horticulture Society (R.H.S.) Colour chart, except where the context indicates a term having its ordinary dictionary meaning. My new tree has not been observed under all growing conditions, and variations may occur as a result of different growning conditions. All the progeny of my new variety, insofar as has been observed, have been identical in all of the characteristics described below.

Other than as set out below, as of this time, no other characteristics have been observed which are different from common Willow Oaks which have been observed by the inventor.

Parentage: Seedling of unknown parentage grown from a seed purchased and planted in 1986 from an unknown source.

Locality where grown and observed: A shopping center parking lot in Athens, Clarke County, Ga.

Leaves: Typical of the species; i.e., alternate, simple, narrowly elliptical, acuminate, acute and tipped with a bristle. The leaves are also entire, and are not often wavy as is sometimes seen in seedling trees. Further, the leaves are typically ⅓"–¾" wide by 2½"–3½" long, medium green color above like RHS 141B and glabrous below like RHS 137D; fall color is typical of the species; yellow-bronze to slightly reddish brown, petiole: light green, ⅛"–¼" long.

Buds: Typical of the species; imbricate, ovoid, and sharp pointed, ⅛"–¼" long, dark brown in color.

Flowers: Typical of the species, monoecious, appearing on old and new growth, staminate catkins are pendant and clustered, individual flowers comprise a 4–7 lobed calyx enclosing 6 or more stamens, pistillate flowers are solitary or in few-to-many clustered spikes from the axils of the new leaves; individual flowers comprise a 6-lobed calyx surrounding a 3-celled ovary the whole of which is partially enclosed in a involucre.

Fruit: An acorn, typical of the species; ovate, ¼"–½" long and wide. The nut is covered only at the base by a short-stalked hemispherical-shaped cap. The fruit has a gray-brown (RHS 199A) hemispherical shaped involucral cap and a gray-orange (RHS 165A) acorn striated with dark brown lines (RHS 200A). Similar to the species in all ways, except observed on the parent to be slightly smaller (about 25% smaller) than that generally of the specices. None of the progeny have yet produced fruit, so it is uncertain whether their trait is inheritable or affected by the parent tree's current growing conditions.

Stem: Typical of the species' slender, smooth, and reddish to dark brown.

Trunk: Typical of the species; mottled gray and black like RHS greyed-green 198D and RHS black 202B and smooth, developing narrow, shallow ridges and furrows with age.

Branching: Very upright ascending branches, emerging at and maintaining an approximately 30° angle from the trunk.

Growth habit: Narrow upright.

Root system: Probably typical of the species; Willow Oak has a more fibrous root system than most other species in the genus and transplants well.

Vigor: Above average. My new tree has outperformed 50% of the other trees planted at the same time at the same site. The progeny have performed better than average compared with the seedling groups.

Diseases: No disease problems have been observed in the parent or any progeny. This is typical of the species.

Pests: No insect problems have been observed on the parent or any progeny. This is typical of the species.

What is claimed is:

1. What is claimed is a new and distinct variety of Willow Oak tree named 'RT3' substantially as shown and described, characterized particularly as to novelty by it narrow, upright, densely branched habit with a central leader.

* * * * *